United States Patent
Shirai et al.

(10) Patent No.: US 11,393,073 B2
(45) Date of Patent: Jul. 19, 2022

(54) MAGNETIC RESONANCE IMAGING APPARATUS AND NOISE ELIMINATION METHOD

(71) Applicant: Hitachi, Ltd., Tokyo (JP)

(72) Inventors: Toru Shirai, Tokyo (JP); Ryota Satoh, Tokyo (JP); Yasuhiro Kamada, Tokyo (JP); Masahiro Takizawa, Tokyo (JP); Yoshihisa Sotome, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 226 days.

(21) Appl. No.: 16/639,407

(22) PCT Filed: Jul. 27, 2018

(86) PCT No.: PCT/JP2018/028301
§ 371 (c)(1),
(2) Date: Feb. 14, 2020

(87) PCT Pub. No.: WO2019/049549
PCT Pub. Date: Mar. 14, 2019

(65) Prior Publication Data
US 2020/0258199 A1    Aug. 13, 2020

(30) Foreign Application Priority Data

Sep. 7, 2017 (JP) .............................. JP2017-172274

(51) Int. Cl.
*G06T 5/00* (2006.01)
*G01R 33/56* (2006.01)
(Continued)

(52) U.S. Cl.
CPC .......... *G06T 5/002* (2013.01); *G01R 33/5608* (2013.01); *G01R 33/56545* (2013.01); *G06T 5/50* (2013.01); *G06T 2207/10088* (2013.01)

(58) Field of Classification Search
CPC . G06T 5/002; G06T 5/50; G06T 2207/10088; G06T 2207/20028;
(Continued)

(56) References Cited

U.S. PATENT DOCUMENTS

| | | |
|---|---|---|
| 7,053,613 B2 | 5/2006 | Lin |
| 2002/0167316 A1 | 11/2002 | King |

(Continued)

FOREIGN PATENT DOCUMENTS

| | | |
|---|---|---|
| JP | 2002-345780 A | 12/2002 |
| JP | 2006-130285 A | 5/2006 |

(Continued)

OTHER PUBLICATIONS

International Search Report (PCT/ISA/210) issued in PCT Application No. PCT/JP2018/028301 dated Oct. 30, 2018 with English translation (four (4) pages).

(Continued)

*Primary Examiner* — Susan S Lee
(74) *Attorney, Agent, or Firm* — Crowell & Moring LLP

(57) ABSTRACT

In an image acquired by a plurality of receiver coils with the use of MRI, separated images are obtained by separating spatially overlapping signals according to PI method, and noise in the separated images is eliminated with a high degree of precision. A complex image spatially overlapping is measured from nuclear magnetic resonance signals received by a plurality of receiver coils, and spatially overlapping signals are separated and a plurality of separated images are calculated, by using sensitivity information of the plurality of receiver coils. Then, noise is eliminated based on a correlation of noise mixed between the separated images.

12 Claims, 13 Drawing Sheets

(51) Int. Cl.
    *G01R 33/565*    (2006.01)
    *G06T 5/50*    (2006.01)

(58) Field of Classification Search
    CPC ...... G06T 2207/20032; G01R 33/5608; G01R 33/56545; G01R 33/4835; G01R 33/546; G01R 33/5611; A61B 5/055
    See application file for complete search history.

(56) References Cited

U.S. PATENT DOCUMENTS

| | | |
|---|---|---|
| 2005/0270024 A1 | 12/2005 | Lin |
| 2009/0206835 A1 | 8/2009 | Nakai |
| 2016/0131730 A1* | 5/2016 | Isogawa ............... G01R 33/565 324/309 |

FOREIGN PATENT DOCUMENTS

| | | |
|---|---|---|
| JP | 2016-93494 A | 5/2016 |
| WO | WO 2006/109550 A1 | 10/2006 |

OTHER PUBLICATIONS

Japanese-language Written Opinion (PCT/ISA/237) issued in PCT Application No. PCT/JP2018/028301 dated Oct. 30, 2018 (three (3) pages).
Pruessmann K. et al., "SENSE: Sensitivity Encoding for Fast MRI", Magnetic Resonance in Medicine, 1999, pp. 952-962, vol. 42, Wiley-Liss, Inc. (11 pages).
Griswold M et al., "Generalized Autocalibrating Partially Parallel Acquisitions (GRAPPA)", Magnetic Resonance in Medicine, 2002, pp. 1202-1210, vol. 47, Wiley-Liss, Inc. (nine (9) pages).
Breuer et al., "Controlled Aliasing in Parallel Imaging Results in Higher Acceleration (CAIPIRINHA) for Multi-Slice Imaging", Magnetic Resonance in Medicine, 2005, pp. 684-691, vol. 53, Wiley-Liss, Inc. (eight (8) pages).
King K. et al., "SENSE Image Quality Improvement Using Matrix Regularization", In Proceedings of the 9th Annual Meeting of ISMRM, Glasgow, Scotland, 2001, p. 1771 (one (1) page).
International Preliminary Report on Patentability (PCT/IB/373) issued in PCT Application No. PCT/JP2018/028301 dated Mar. 10, 2020, Including English translation of document C2 (Japanese-language Written Opinion (PCT/ISA/237), filed on Feb. 14, 2020) (five (5) pages).

* cited by examiner

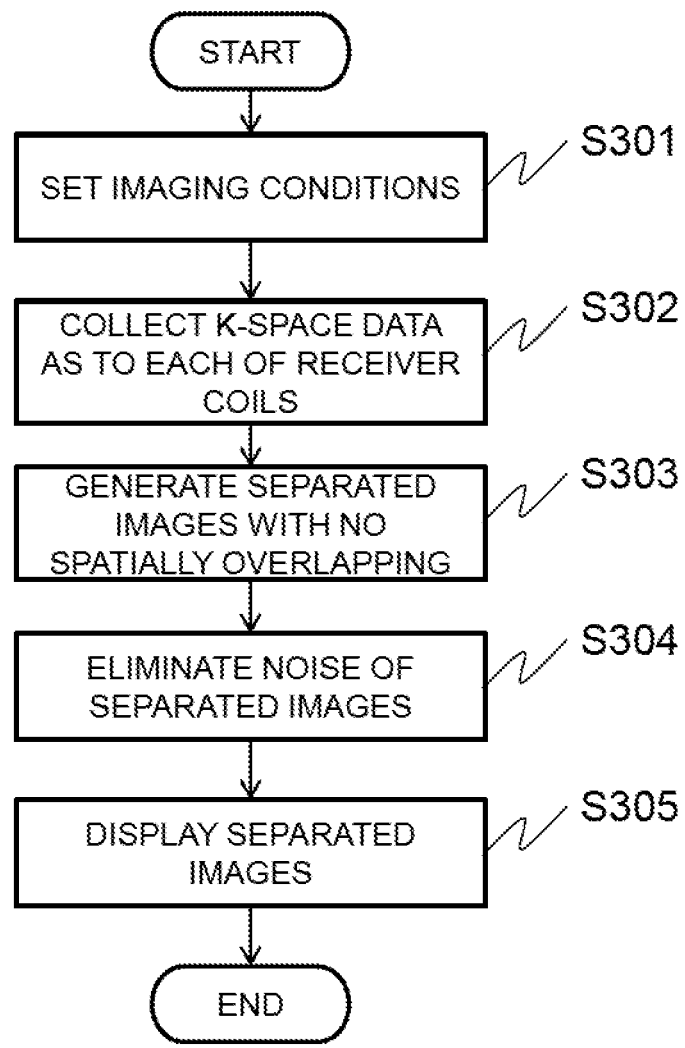

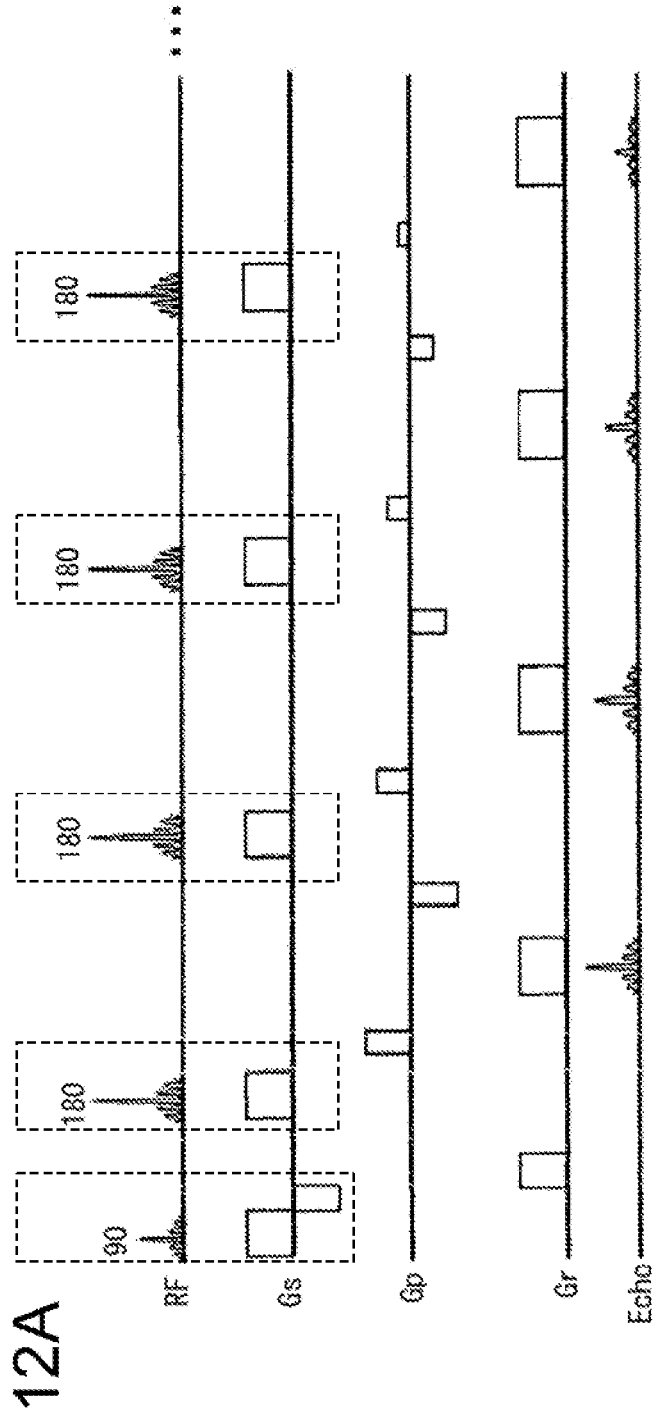
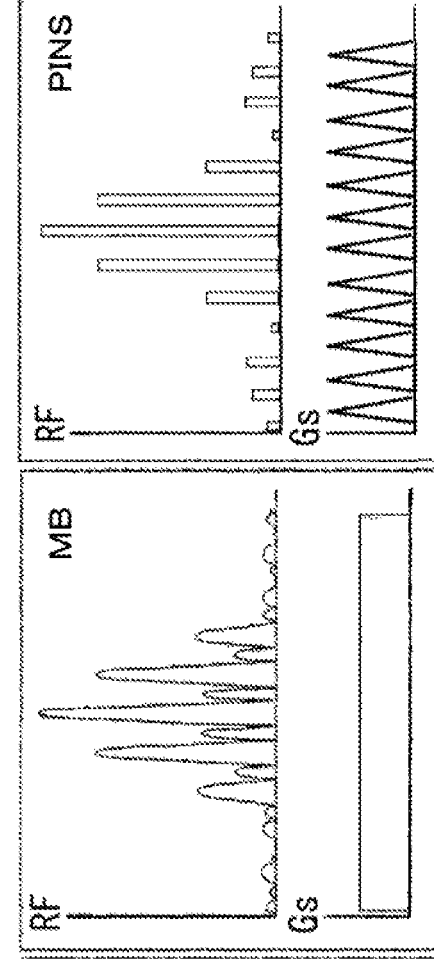
FIG. 12A
FIG. 12B
FIG. 12C

MAGNETIC RESONANCE IMAGING APPARATUS AND NOISE ELIMINATION METHOD

TECHNICAL FIELD

The present invention relates to a magnetic resonance imaging (MRI) technique. More particularly, it relates to an image processing technique for eliminating noise from an image where spatially overlapping signals are separated, in images acquired by a plurality of receiver coils.

BACKGROUND ART

A magnetic resonance imaging (MRI) apparatus is non-invasive medical image diagnostic equipment utilizing a nuclear magnetic resonance phenomenon where hydrogen nuclei (protons) placed in a static magnetic field are resonated with an RF magnetic field at a specific frequency. The MRI is capable of taking images of various tissue contrast with changes of an imaging method or imaging parameters, and this allows acquisition of, not only morphological information but also information relating to a living body such as bloodstream and metabolic functions. Thus the MRI is indispensable for a field of diagnostic imaging.

One of technical issues of the MRI is a shortening reduction of imaging time. Methods for shortening imaging-time in the MRI includes high-speed scanning of k-space such as Echo Planar Imaging (EPI) and Fast Spin Echo (FSE), and measuring a few points in k-space to reconstruct unmeasured points by signal processing, such as SENSE method (e.g., Non Patent Literature 1) and GRAPPA method (e.g., Non Patent Literature 2). There is also another imaging-time shortening method in two-dimensional (2D) multi-slice measurement where a plurality of slices is imaged simultaneously, and overlapping signals are separated by signal processing, such as CAIPIRINHA method (e.g., Non Patent Literature 3). In those methods such as the EPI method and the FSE method, image contrast being obtained is limited, and in addition, it is susceptible to static magnetic field inhomogeneity and T2 attenuation. On the other hand, the SENSE method, GRAPPA method, and CAIPIRINHA method (hereinafter, collectively referred to as Parallel Imaging (PI) method), have a characteristic that can shorten the imaging time irrespective of an imaging sequence.

According to the PI method, a plurality of receiver coils acquire spatially overlapping signals, and the spatially overlapping signals are separated by using a difference in sensitivity distribution between the receiver coils. A signal-to-noise ratio (SNR) of the image after the separation (separated image) made up of signals separated by the PI method is known to be inversely proportional to an index referred to as Geometry factor (g-factor). When the difference in sensitivity between the receiver coils is small at the position of signals spatially overlapping, the g-factor is increased, whereas the SNR is reduced.

In order to prevent the SNR reduction due to the increase of the g-factor, there are suggested various methods. As a representative method, there are disclosed a noise elimination method using regularization (e.g., Non Patent Literature 4), and noise elimination method combining a reference image and regularization (e.g., Patent Literature 1).

CITATION LIST

Patent Literature

Patent Literature 1
U.S. Pat. No. 7,053,613 SPECIFICATION

Non Patent Literature

Non Patent Literature 1
Pruessmann K P et al., SENSE: Sensitivity Encoding for Fast MRI", Magnetic Resonance in Medicine, 1999, vol. 42, pp. 952-962
Non Patent Literature 2
Griswold M A et al., "Generalized Autocalibrating Partially Parallel Acquisitions (GRAPPA)", Magnetic Resonance in Medicine, 2002, vol. 47, pp. 1202-1210
Non Patent Literature 3
Felix A B et al., "Controlled Aliasing in Parallel Imaging Results in Higher Acceleration (CAIPIRINHA) for Multi-Slice Imaging", Magnetic Resonance in Medicine, 2005, vol. 53, pp. 684-691
Non Patent Literature 4
King K F et al., "SENSE Image Quality Improvement Using Matrix Regularization", In Proceedings of the 9th Annual Meeting of ISMRM, Glasgow, Scotland, 2001, p. 1771

DISCLOSURE OF THE INVENTION

Problems to be Solved by the Invention

According to the method described in Non Patent Literature 4, prior information referred to as Zeroth Order Regularization combined with a process for separating the sensitivity by using a difference in sensitivity distribution between the receiver coils, is applied to spatially overlapping signals, whereby separated images with reduced noise can be obtained. However, the method of Non Patent Literature 4 has a problem that an effect of noise reduction is low, because the prior information included in the regularization does not represent characteristics between the spatially overlapping signals.

According to the method described in Patent Literature 1, prior information referred to as Tikhonov regularization, reference images not overlapping spatially, and a process for separating the sensitivity by using a difference in sensitivity distribution between the receiver coils, are combined and applied to spatially overlapping signals, whereby separated images with reduced noise can be obtained. However, the method described in Patent Literature 1 requires measurement of the reference images not overlapping spatially in advance, in addition to the reception sensitivity distribution, and thus, the imaging time tends to be extended.

The present invention has been made in view of the situations as described above, and an objective of the present invention is to provide a technique for eliminating noise of the separated images obtained by separating spatially overlapping signals according to the PI method, in the images acquired by a plurality of the receiver coils, without the necessity for an additional reference image.

Means for Solving the Problems

According to the present invention, sensitivity distributions of a plurality of receiver coils are used to calculate a plurality of separated images obtained by separating spatially overlapping signals, from nuclear magnetic resonance signals received by the plurality of receiver coils. Then, noise is eliminated on the basis of a correlation of noise mixed between the separated images. The spatially overlapping signals represent signals (superimposed signals) that are overlapping one another in the state each of the signals from different positions cannot be identified by the signal itself. The spatially superimposed signals described in the present specification includes not only superimposed signals in the image space, but also signals in k-space that become the spatially superimposed signals when an image is reconstructed.

In other words, an MRI apparatus according to the present invention comprises, a measuring part that includes a transmission part configured to transmit an RF (Radio Frequency) pulse to a subject placed in a static magnetic field, a reception part configured to receive nuclear magnetic resonance signals generated from the subject by a plurality of receiver coils, and a gradient magnetic field generator configured to provide a gradient magnetic field to the static magnetic field, and a computer configured to perform computations on the nuclear magnetic resonance signals thus received, wherein the computer comprises an image generator configured to process the nuclear magnetic resonance signals received by the plurality of receiver coils to generate a plurality of separated images not spatially overlapping one another, by using sensitivity information of the plurality of receiver coils, and a noise eliminator configured to eliminate noise from each of the separated images, on the basis of a correlation of noise mixed between the separated images.

Advantages of the Invention

A high quality noise-eliminated image can be computed, without imaging references images or a similar image for eliminating noise. This prevents extension of total imaging time, and diagnostic precision can be improved.

BRIEF DESCRIPTION OF THE DRAWINGS

FIG. 2A illustrates an MRI apparatus of vertical magnetic field type, FIG. 2B illustrates an MRI apparatus of horizontal magnetic field type, and FIG. 2C illustrates an MRI apparatus enhancing the sense of openness;

FIG. 3 is a flowchart showing one embodiment of a processing according to a computer;

FIG. 4A illustrates the noise correlation of a real part of a complex image, and FIG. 4B illustrates the noise correlation of an imaginary part of the complex image;

FIG. 12A illustrates one example of the pulse sequence employed in a second embodiment, FIGS. 12B and 12C illustrate essential portions thereof.

BEST MODE FOR CARRYING OUT THE INVENTION

There will now be described embodiments of an MRI apparatus to which the present invention is applied.

[Overview of MRI Apparatus]

Figure 1:
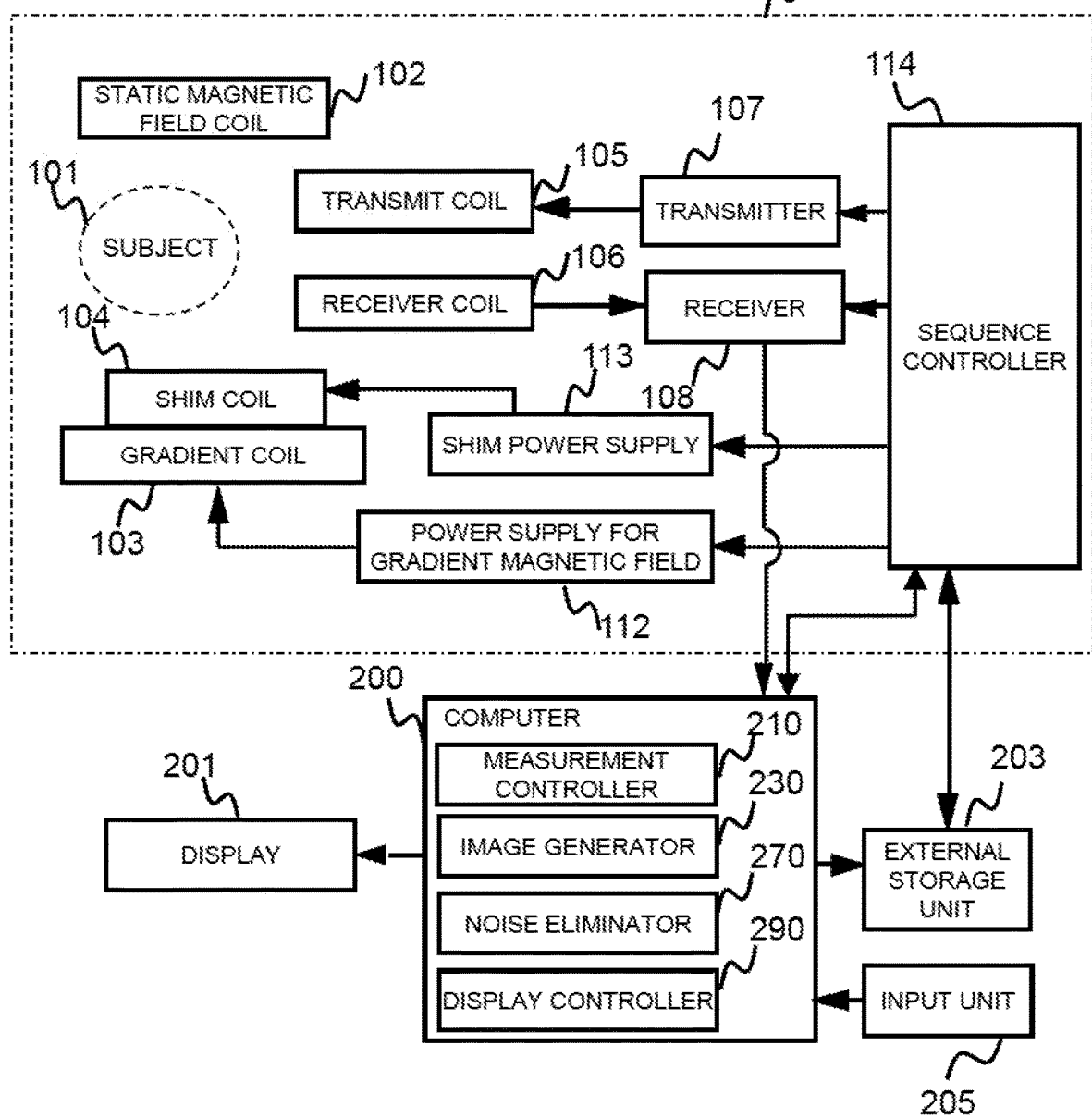
FIG. 1 is a block diagram shown a schematic configuration of an MRI apparatus according to an embodiment of the present invention.

As shown in FIG. 1, the MRI apparatus according to the present embodiment comprises broadly, a measuring part 100 configured to measure nuclear magnetic resonance signals generated from a subject 101, and a computer 200 configured to control the measuring part 100, and to perform image reconstruction, correction, and other computations by using the nuclear magnetic resonance signals measured by the measuring part 100.

The measuring part 100 is provided with a static magnetic field coil 102 configured to generate a static magnetic field in the space where the subject 101 is placed, a transmission part (105, 107) configured to transmit an RF pulse to the subject 101 placed within the static magnetic field, a reception part (106, 108) configured to receive nuclear magnetic resonance signals generated from the subject, and a gradient coil 103 configured to provide magnetic gradient to the static magnetic field generated from the static magnetic field coil 102, in order to give positional information to the nuclear magnetic resonance signals.

Figure 2A:
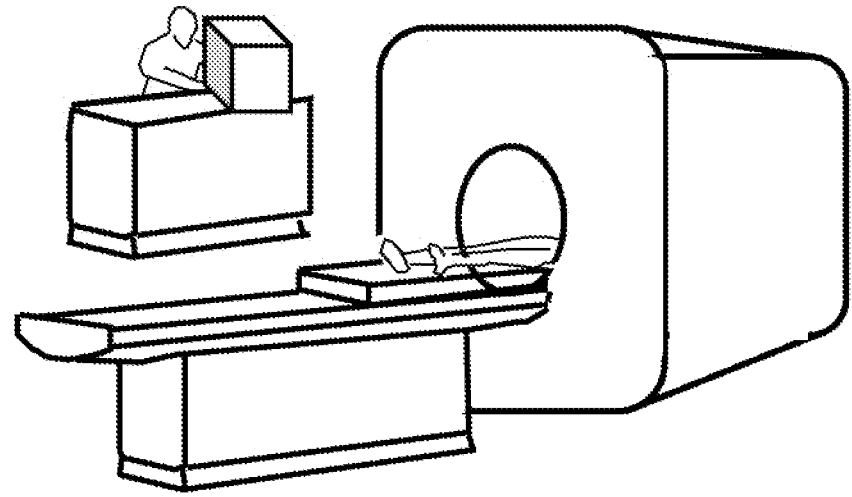
FIGS. 2A to 2C are external views of the MM apparatus to which the present invention is applied.
Figure 2B:
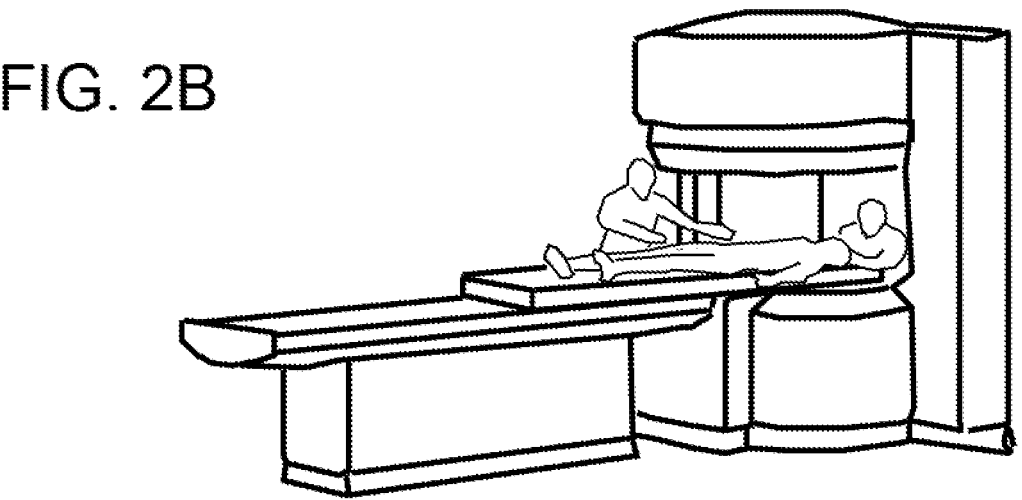
Figure 2C:
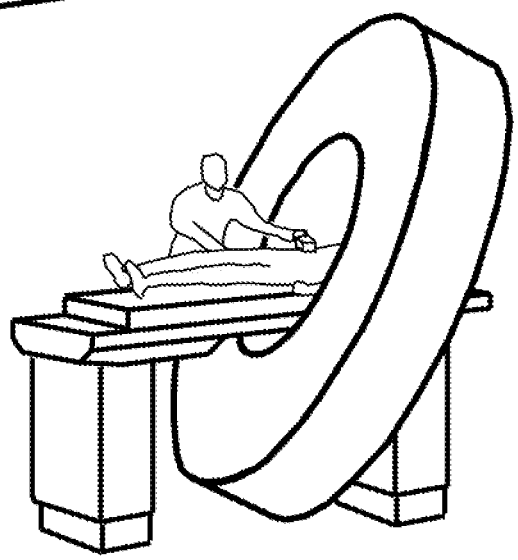

The static magnetic field coil 102 comprises a normal conductive-type or superconductive-type static magnetic field coil, a magnet for generating static magnetic field, and others, and the direction of generated static magnetic field determines a mode, a vertical magnetic field mode or a horizontal magnetic field mode, and depending on the mode, the shape of the coil and an external view of the entire apparatus are different. FIGS. 2(a) to 2(c) illustrate external views of various types of the MRI apparatus different in the mode. The present embodiment is applicable to any of the illustrated types of the MRI apparatus.

The transmission part is provided with a transmit RF coil 105 (hereinafter, simply referred to as "transmit coil") configured to transmit an RF magnetic field to a measurement area of the subject 101, and a transmitter 107 provided with an RF oscillator, an amplifier, and others. The reception part is provided with a receiver 108 including a receive RF coil 106 (hereinafter, simply referred to as "receiver coil") configured to receive nuclear magnetic resonance signals generated from the subject 101, a quadrature detector, an A/D converter, and others. In the present embodiment, the receiver coil comprises a plurality of channels (small receiver coils), and the quadrature detector and the A/D converter incorporated in the receiver 108 are connected to each of the channels. The nuclear magnetic resonance signals received by the receiver 108 are passed to the computer 200, in the form of complex digital signals. In the present embodiment, spatially overlapping signals are measured and those signals are separated in a reconstructed image. In the separation, sensitivity distributions of the receiver coils are used, which receive the magnetic resonance signals generated from the subject 101. For this purpose, in the present embodiment, the number of the receiver coils 106 is at least equal to or more than the number of signals being separated.

The gradient coil 103 includes three gradient coils to apply gradient magnetic fields to x-direction, y-direction, and z-direction, respectively, and each of the gradient coils is connected to the power supply for the gradient magnetic field 112. Furthermore, the MRI apparatus may be provided with a shim coil 104 for adjusting a static magnetic field distribution, and a shim power supply 113 for driving the shim coil.

The measuring part 100 is further provided with a sequence controller 114 configured to control operations of the measuring part 100. The sequence controller 114 controls the operations of the power supply for the gradient magnetic field 112, the transmitter 107 and the receiver 108, and further controls the timing for applying the gradient magnetic field and the RF magnetic field and for receiving the nuclear magnetic resonance signals. The time chart for the control is referred to as a pulse sequence, and it is preset in response to the measurement and stored in a storage unit and the others, provided in the computer 200 described below.

The computer 200 controls the entire operations of the MRI apparatus 100, and performs various computing operations on the received nuclear magnetic resonance signals. The computer 200 is an information processor provided with a CPU, a memory, the storage unit, and others. The computer 200 is connected to a display 201, an external storage unit 203, an input unit 205, and so on.

The display 201 is an interface to present results for an operator, the results being obtained by the computing process. The input unit 205 is an interface prompting the operator to enter conditions, parameters, and others, necessary for the measurement and the computing process performed in the present embodiment. The user is allowed to enter measurement parameters, for example, such as the number of times speed in a PI (Parallel Imaging) method, via the input unit 205. The external storage unit 203, together with the storage unit within the computer 200, holds data used in various computations executed by the computer 200, data obtained by the computations, inputted conditions and parameters, and others.

In the present embodiment, the computer 200 generates sensitivity distributions of the receiver coils, separated images, a noise eliminated image, and others. Therefore, as shown in FIG. 1, the computer 200 is provided with functional parts, such as a measurement controller 210, an image generator 230, a noise eliminator 270, and a display controller 290. Functions of those parts are implementable in the form of software incorporated in the computer 200, and they are implemented when the CPU loads the programs (software) held in the storage unit and executes the programs. Various data used in the processing of each function, and various data generated during the processing, are stored in the storage unit or in the external storage unit 203. In addition, another information processor independent of the MRI apparatus 10, data being transmittable and receivable with the MRI apparatus 100, may implement at least one of the various functions implemented by the computer 200. All or apart of the functions may be implemented by hardware such as ASIC (Application Specific Integrated Circuit) and FPGA (field-programmable gate array).

Next, there will be described an overview of operations of the MRI apparatus (mainly, the computer 200) according to the present embodiment. FIG. 3 shows the details of the processing.

First, settings such as an imaging sequence and imaging conditions, configured by a user, are accepted via the input unit 115 (S301). The imaging sequence is not limited, but in the present embodiment, in order to reduce the imaging time, an imaging method (PI method) for measuring spatially overlapping signals is selected and settings for this method are configured. The imaging conditions include parameters of the imaging sequence (repetition time TR and echo time TE), and a thinning rate (reduction factor) is included if the thinning measurement (under-sampling) in k-space is performed. In the case of SMS (Simultaneous Multi-Slice), settings of the number of slices are also included. When the imaging conditions and others are configured as examination protocols, conditions and other information defined in the examination protocols are read in.

The spatially overlapping signals indicate signals coming from different positions in real space, overlapping one another without encoded by the gradient magnetic field. These signals may include signals spatially overlapping after under-sampling is performed (signals containing so-called aliasing), and signals from the simultaneous multi-slice (SMS). The measurement method determines what type is the "spatially overlapping signal".

The measurement controller 210 allows the sequence controller 114 to operate according to the pulse sequence configured on the basis of the parameters entered by the user, and measures nuclear magnetic resonance signals (echo signals) under a predetermined condition. The sequence controller 114 controls each part of the MRI apparatus 100 according to an instruction from the measurement controller 210, and measures the spatially overlapping signals so as to reduce the imaging time (S302). That is, k-space data is collected with respect to each receiver coil. The image generator 230 separates the spatially overlapping signals to form a plurality of images (separated images) at spatially different positions, by using the k-space data as to each of the receiver coils and sensitivity distributions of a plurality of receiver coils (S303).

Next, the noise eliminator 270 removes noise on the basis of a correlation of noise included in each of the separated images (S304). Noise elimination is implemented by performing an iterative operation for minimizing noise under predetermined constraints, similar to the publicly known non-linear filters such as TotalVariation regularization and sparse regularization. The noise eliminator 270 of the present embodiment performs the iterative operation that includes as a constraint, the noise correlation between separated images.

Figure 4A:
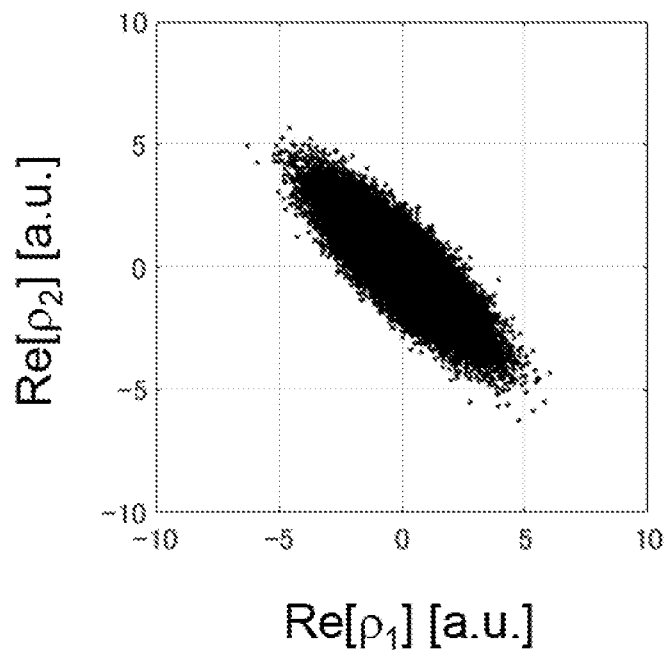
FIGS. 4A and 4B illustrate noise correlations.
Figure 4B:
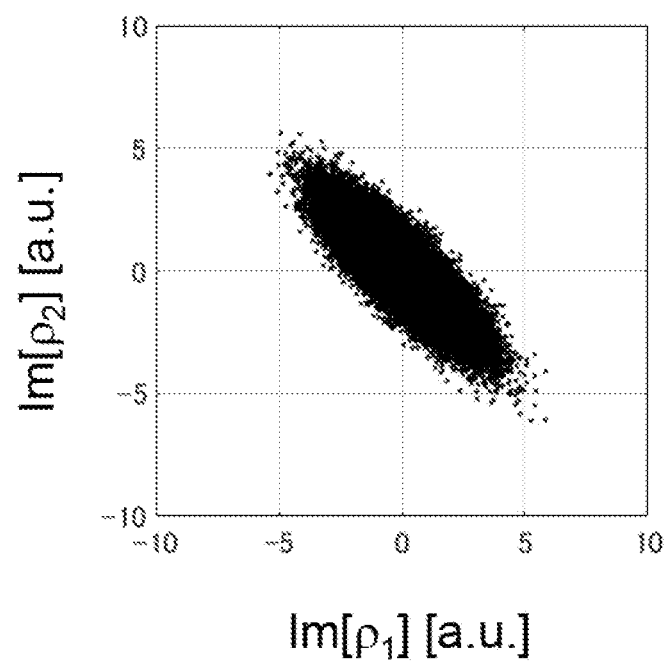

There will be described the noise correlation between separated images, using computer simulation. FIG. 4 shows a specific example of the noise correlations obtained by the simulation. In this example, the sensitivity distributions of 15-channel receiver coils were used, being calculated by measuring a human head part, and complex noise images corresponding to 15 channels, uncorrelated with one another, were created. These complex noise images were combined, modeled into two complex images overlapping each other, and two separated images were obtained by using the sensitivity distributions of the 15-channel receiver coils. FIGS. 4(a) and 4(b) show results of plotting signals, respectively, of the real part and the imaginary part of the separated two images $\rho_1$ and $\rho_2$, where the horizontal axis represents $\rho_1$ and the vertical axis represents $\rho_2$. As shown in FIG. 4, it is found that there was negative correlation between the images $\rho_1$ and $\rho_2$ after separating the complex noise images, in any of the real part and the imaginary part. In other words, variance of the sum of the separated images $\rho_1$ and $\rho_2$ was found to be smaller than the variance before the separation.

Figure 5:
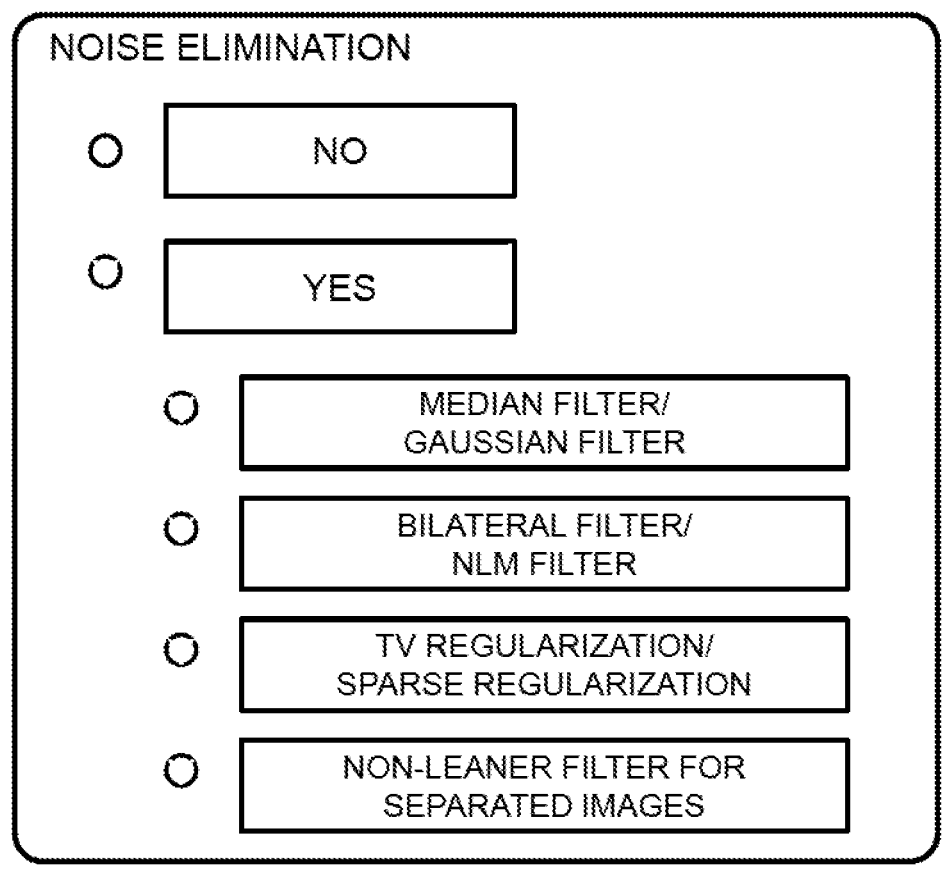
FIG. 5 illustrates one example of UI for selecting a noise elimination method.

In the aforementioned condition setting step S301, user selection of the noise elimination method can be accepted, and in that case, for example, the display controller 290 presents the UI as shown in FIG. 5 on the display 201. In the example as illustrated, the noise elimination method of the present embodiment is made selectable, in addition to the publicly known noise elimination methods, for example, a linear filter such as a median filter and Gaussian filter, an edge preserving filter such as Bilateral filter, and a non-linear filter such as TotalVariation regularization and sparse regularization. This configuration enhances flexibility in user's method selection. The separated images after noise is eliminated are stored in the storage unit 203 as required, or presented on the display 201 (S305).

According to the present embodiment, multiple receiver coils are used to acquire spatially overlapping signals. Then, those signals are separated into a plurality of images (separated images) not overlapping spatially, by using the sensitivity distribution of each of the receiver coils, and noise in the separated images is removed by using the noise correlation between the separated images as the constraints. Using the noise correlation between the separated images as constraints for the noise elimination process, allows highly accurate noise elimination, specialized in eliminating noise in the separated images.

There will be described in detail the processing of the embodiment according to measuring method. The overview of the MRI apparatus as shown in FIG. 1 is common to all the embodiments and referred to as required.

First Embodiment

In the present embodiment, a 2D parallel imaging method that performs under-sampling in the phase encoding direction is employed. Further in the present embodiment, spatially overlapping signals are separated according to the SENSE method. In other words, the k-space data collected as to each of the receiver coils is subjected to image reconstruction, and then, separated images are generated by computations from thus obtained images.

Figure 6:
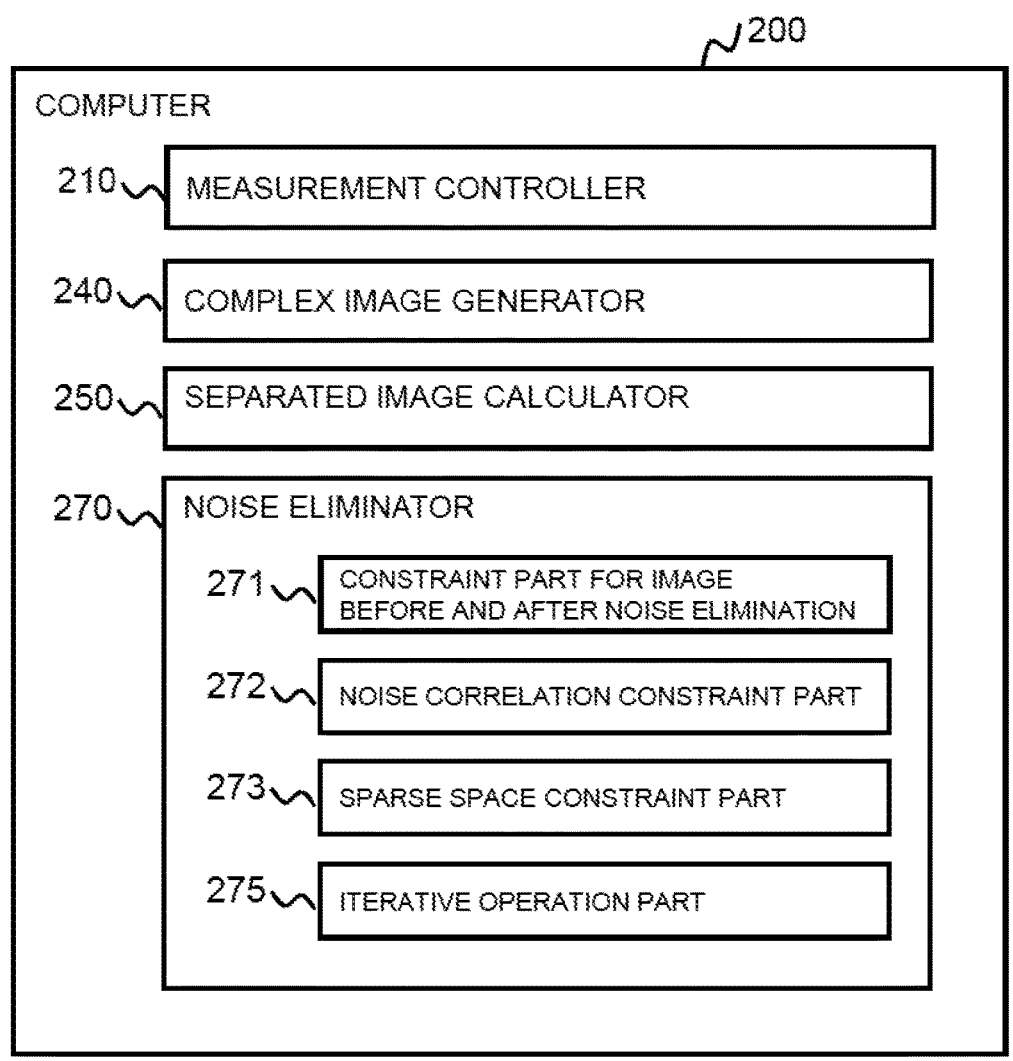
FIG. 6 is a functional block diagram of the computer according to a first embodiment.

FIG. 6 shows a configuration of the computer 200 according to the present embodiment. In FIG. 6, an element having a function identical to the function shown in FIG. 1 is labeled with the same reference numeral, and they will not be redundantly explained. As illustrated, in the present embodiment, the image generator 230 includes a complex image generator 240 and a separated image calculator 250. In addition, the noise eliminator 270 is provided with an iterative operation part 275 for executing the iterative operation, and a plurality of constraint parts (271 to 273) for setting the constraints in the iterative operation.

Figure 7:
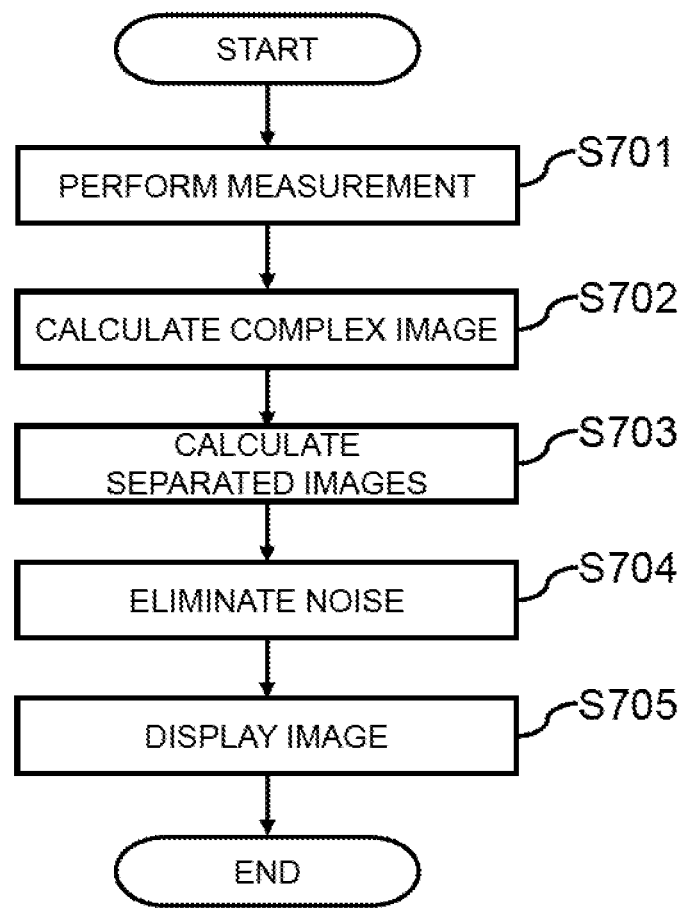
FIG. 7 is a flowchart showing a processing of the computer according to the first embodiment.

Hereinafter, with reference to the flowchart of FIG. 7, functions and actions of each part in the computer 200 will be described.

[Perform Measurement: S701]

The measurement controller 210 activates the sequence controller 114 according to the pulse sequence configured on the basis of the parameters entered by a user via an input unit 115. Then, nuclear magnetic resonance signals (echo signals) under predetermined conditions are measured.

The pulse sequence used by the measurement controller 210 is not particularly limited. However, in this example, there will be described the case where a 2D-GrE type pulse sequence is used to perform imaging at a thinning rate 1/2 (reduction factor is 2).

Figure 8:
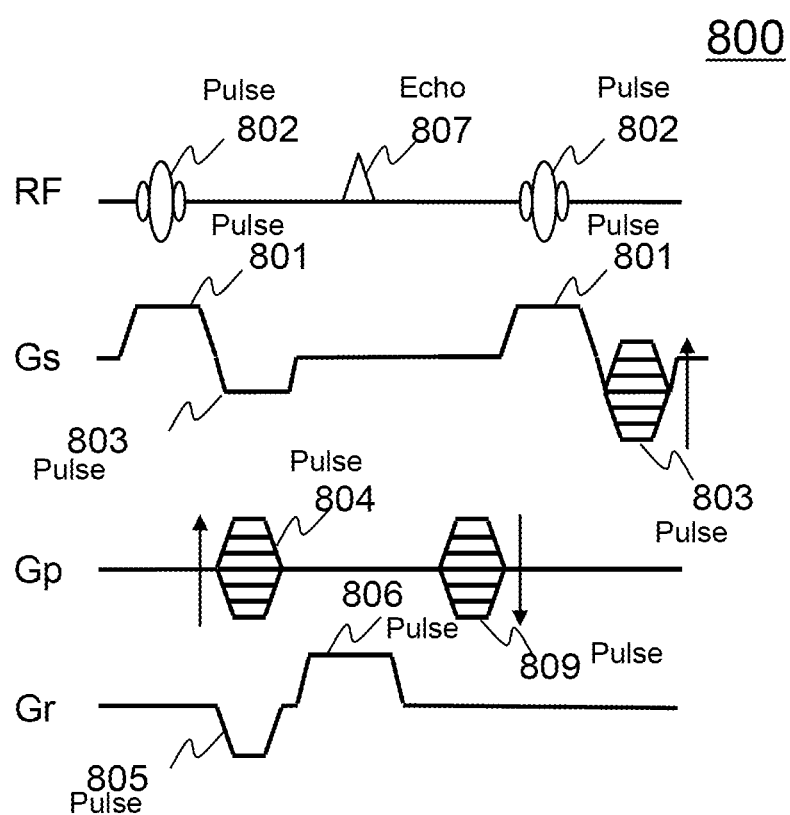
FIG. 8 shows one example of a pulse sequence employed in the first embodiment.

FIG. 8 shows a 2D-RSSG (RF-spoiled-Steady-state Acquisition with Rewound Gradient-Echo) sequence 800 as an example of the 2D-GrE type pulse sequence. In this figure, RF, Gs, Gp, and Gr represent, respectively, an RF magnetic field, a slice gradient magnetic field, a phase encoding gradient magnetic field, and a readout gradient magnetic field.

In the RSSG sequence 800, an RF magnetic field (RF) pulse 802 is applied with application of a slice gradient pulse 801, thereby exciting magnetization of a given slice within the subject 101. Then, together with application of a rephase slice gradient pulse 803 that allows convergence of magnetization phase having been dispersed along with applying the slice gradient pulse 801, a phase encoding gradient pulse 804 is applied for adding positional information in the phase encoding direction.

After applying a readout gradient pulse for dephasing 805 that disperses the nuclear magnetizing phase within a pixel, a nuclear magnetic resonance signal (echo) 807 is measured while applying the readout gradient pulse 806 for adding the positional information in the readout direction. Finally, a phase encoding gradient pulse for rephasing 809 is applied for convergence of magnetizing phase that has been dephased by the phase encoding gradient pulse 804.

The measurement controller 210 repeatedly executes the procedures above every repetition time TR, while varying the strength of the phase encoding gradient pulses 804 and 809 (the number of phase encoding kp) and the phase of the RF pulse 802, whereby echoes necessary for obtaining one image are measured. At this time, in order to perform double-speed measurement in the phase encoding direction, the measurement is performed with the number of the phase encoding kp determined by an FOV, taking every other phase encoding number. Accordingly, the imaging time can be reduced to half. In addition, the phase of the RF pulse 802 is incremented by 117 degrees every repetition, for instance. In FIG. 8, the number following the hyphen indicates the number of repetitions.

[Calculate Complex Image: S702]

Figure 9:
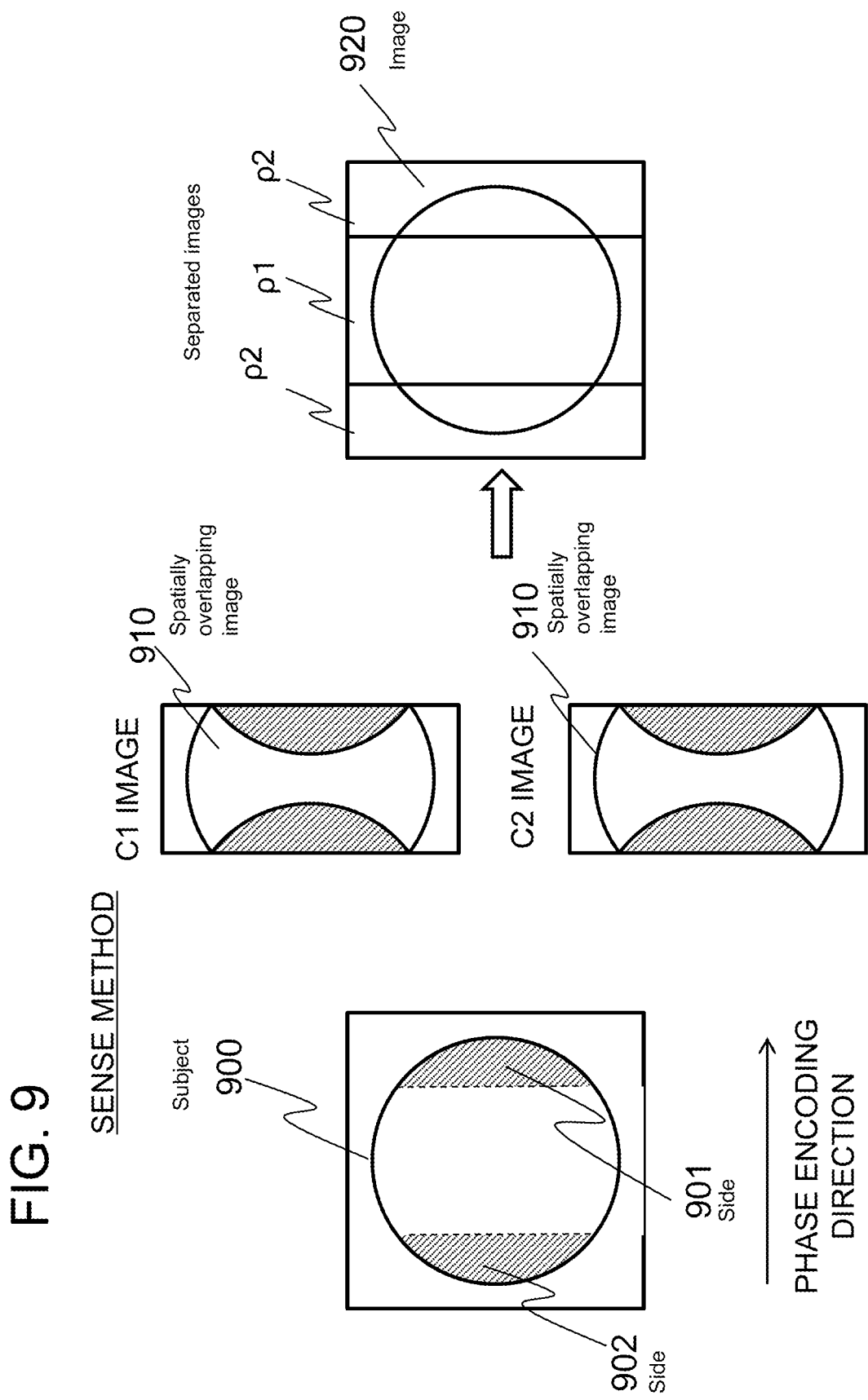
FIG. 9 illustrates one example of spatially overlapping signals according to the first embodiment.

The complex image generator 240 places in k-space, each of the echo signals measured by a plurality of receiver coils in S701, and k-space data is obtained. Then, this k-space data is subjected to the Fourier transform, whereby a complex image is calculated. As shown in FIG. 9, for example, in the complex image thus obtained, each of the areas on the both sides (diagonally shaded areas) 901 and 902 in the phase encoding direction of the subject 900 is folded on the other side (the right-side area is folded on the left side, and the left-side area is folded on the right side), and spatially overlapping image 910 is obtained. In the figure, images of two receiver coils C1 and C2 are shown.

[Calculate Separated Images: S703]

The separated image calculator 250 separates the spatially overlapping complex image, by using sensitivity distributions of the plurality of receiver coils. Signals $S_m$ of the images generated from the receive coils m are given by the following equation (1) where a signal of the separated image at the position n (n is an integer from 1 to N:N is the number of image overlapping, i.e., the reduction factor, which is "2 (double)" in this example) is $\rho_n$, and the sensitivity of the receive coil m (m is an integer from 1 to M) at the position n is $C_{mn}$:

[Equation 1]

$$\begin{bmatrix} S_1 \\ S_2 \\ \vdots \\ S_M \end{bmatrix} = \begin{bmatrix} C_{11} & C_{12} & \ldots & C_{1n} \\ C_{21} & C_{22} & \ldots & C_{2n} \\ \vdots & \vdots & \ddots & \vdots \\ C_{M1} & C_{M2} & \ldots & C_{MM} \end{bmatrix} \begin{bmatrix} \rho_1 \\ \rho_2 \\ \vdots \\ \rho_N \end{bmatrix} \quad (1)$$

Assuming the vectors and the matrix in Equation (1) are vector ρ, matrix C, and vector S, the vector ρ can be calculated from Equation (2):

[Equation 2]

$$\rho = (C^H \Psi^{-1} C)^{-1} C^H \Psi^{-1} S \qquad (2)$$

where the matrix $C^H$ represents the complex conjugate transpose of a matrix of the sensitivity matrix C, and the matrix Ψ represents noise correlation matrix between the receiver coils. For example, when the signals measured at double speed (N=2) in the SENSE method are separated according to the number of the receiver coils 2 (M=2), the vector ρ is 2×1 vector, the sensitivity matrix C is 2×2 matrix, and the vector S is 2×1 vector.

According to Equation (2), the spatially overlapping images $\rho_1$ and $\rho_2$ can be separated. That is, the image 920 as shown in FIG. 9 can be obtained.

[Noise Elimination: S704]

The noise eliminator 270 performs the noise elimination process according to an iterative operation (repetitive process). The noise elimination process uses a correlation of noise mixed into the images $\rho_1$ and $\rho_2$ separated by the separated image calculator 250. The correlation of the noise mixed into the separated images $\rho_1$ and $\rho_2$ can be obtained in advance according to the computer simulation, for instance. In addition, as shown in FIG. 4, the noise correlation is negative, and variance of the sum of the images $\rho_1$ and $\rho_2$ after the separation is smaller than the variance before the separation.

Namely, the noise eliminator 270 uses a constraint (hereinafter, referred to as "noise correlation constraint"), as a constraint of the iterative operation, indicating that a sum image of the separated images before noise elimination is nearly equal to a sum image of the separated images after noise elimination.

Preferably, general conditions as constraints for noise elimination may be added to the noise eliminator 270, in addition to the noise correlation constraint. Specifically, the general conditions may include a constraint that the separated images before noise elimination are nearly equal to the images after noise elimination (hereinafter, referred to as "constraint for image before and after noise elimination), and a constraint indicating that noise of the image obtained by mapping the separated image in sparse space is nearly equal to zero (hereinafter, referred to as "sparse space constraint"). Therefore, the noise eliminator 270 is provided with a constraint part for image before and after noise elimination 271, a noise correlation constraint part 272, and a sparse space constraint part 273, and these constraint parts are configured to generate the constraints, respectively.

Figure 10:
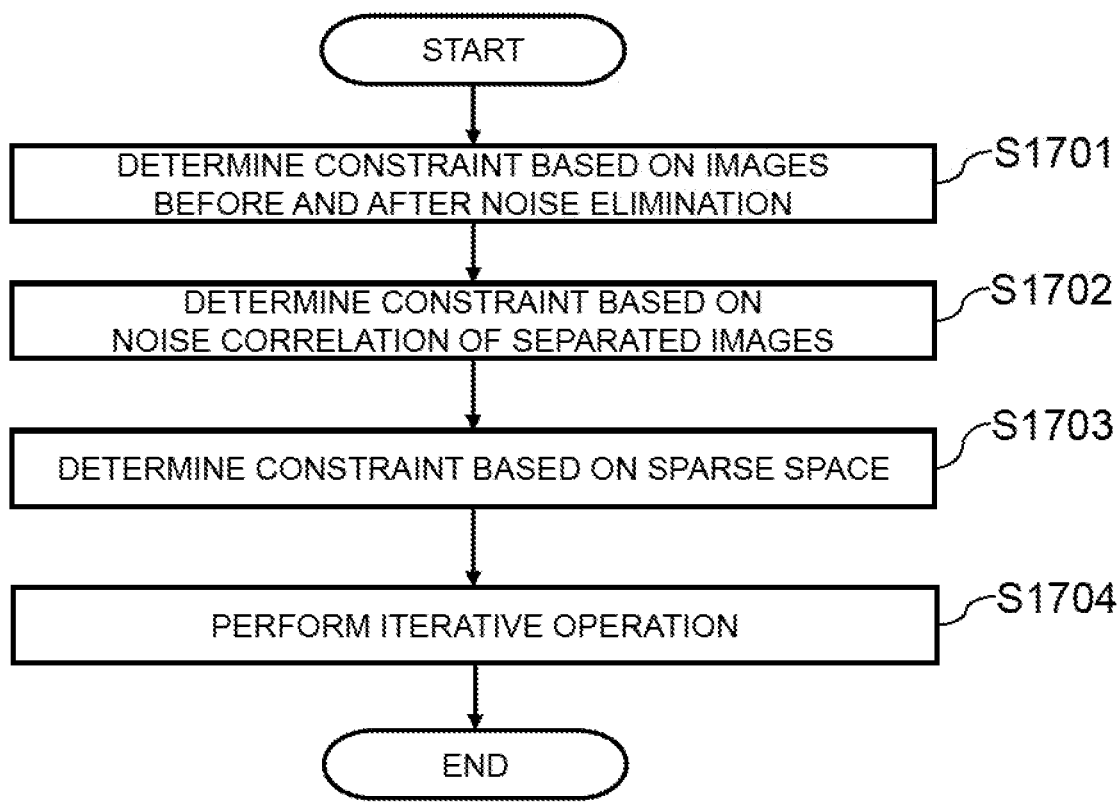
FIG. 10 is a flowchart showing a processing of a noise eliminator according to the first embodiment.

There will be described the noise processing (S704) that includes generation of such constraints. FIG. 10 is a flowchart of the noise processing. First, the constraint part for image before and after noise elimination 271 generates a function representing the constraint for image before and after noise elimination (S1701). Next, the noise correlation constraint part 272 generates a function representing the constraint (noise correlation constraint) that the sum image of the separated images before noise elimination is nearly equal to the sum image of separated images after noise elimination (S1702). Then, the sparse constraint part 273 generates a function representing the sparse space constraint (S1703). Finally, the constraint part for image before and after noise elimination 271, the noise correlation constraint part 272, and the sparse space constraint part 273 are combined to perform the processing of the iterative operation (S1704).

There will be described each processing in detail.

[Determine Constraint Based on Image Before and After Noise Elimination: S1701]

The constraint part for image before and after noise elimination 271 generates the function $E_1(I_1, I_2)$ defined by Equation (3) where the separated images before noise elimination are $\rho_1$ and $\rho_2$, and the separated images after noise elimination are $I_1$ and $I_2$:

[Equation 3]

$$E_1(I_1, I_2) = \sum_{i=1}^{2} \|M_i(\rho_i - I_i)\|_2^2 \qquad (3)$$

where $M_i$ is a weighted image.

In the present embodiment, a binary mask is used, setting a sensitivity area of the receiver coil to 1, and the area other than the sensitivity area to 0. The function $E_1(I_1, I_2)$ of Equation (3) represents the constraint (hereinafter, referred to as "before and after image constraint") indicating that the separated images $I_1$ and $I_2$ after the noise elimination do not move away from the images $\rho_1$ and $\rho_2$ before noise elimination, due to excessive noise elimination process.

[Determine Constraint Based on Noise Correlation of Images After Separation: S1702]

Next, the noise correlation constraint part 272 generates a function $E_2(I_1, I_2)$ defined by Equation (4):

[Equation 4]

$$E_2(I_1, I_2) = \left\| \sum_{i=1}^{2} W_i(\rho_i - I_i) \right\|_2^2 \qquad (4)$$

where $W_i$ is a weighted image.

In the present embodiment, a g-factor map is used as the weighted image, for instance. The g-factor can be obtained by using the sensitivity distributions of the receiver coils and the noise correlation matrix between receptions.

It is to be noted that the weighted image $W_i$ is not limited to the aforementioned one. For example, a freely selected threshold Th is provided to use a weight obtained by subtracting the threshold Th from the g-factor map. When the value of $W_i$ is smaller than zero, it is set to zero. This allows the noise correlation constraint to act on only the area where the separated images $I_1$ and $I_2$ are overlapping. As an alternative weight, the binary mask $M_i$ employed in Equation (3) may also be used. Function $E_2(I_1, I_2)$ of Equation (4) represents the constraint indicating that a sum of noise in the separated images $I_1$ and $I_2$ before noise elimination is nearly equal to the sum of noise in the separated images $I_1$ and $I_2$ after noise elimination, according to the noise correlation after the separation. In other words, this function indicates that the noise elimination does not affect the summing relation of the separated images after the separation (hereinafter, referred to as "noise correlation constraint").

[Determine Constraint Based on Sparse Space: S1703]

Next, the sparse constraint part 273 generates the function $E_3(I_1, I_2)$ defined by Equation (5).

[Equation 5]

$$E_3(I_1, I_2) = \sum_{i=1}^{2} A_i \|\Phi(I_i)\|_1 \qquad (5)$$

where $\Phi$ represents the sparse space mapping operator for mapping an image in the sparse space.

In the present embodiment, Wavelet transform is used, for instance. In addition, $\|\cdot\|_1$ represents L1 norm. The weighted image is represented by $A_i$. In the present embodiment, for example, the g-factor is used as the weighted image. The weighted image $A_i$ is not limited to those as described above, and the binary mask $M_i$ used in Equation (3) may be employed. Function $E_3(I_1, I_2)$ of Equation (5) represents the constraint (hereinafter, referred to as "sparse space constraint") that is provided to make the image mapped in the sparse space according to Wavelet transform be a sparser image according to L1 norm.

[Iterative Operation: S1704]

The iterative operation part 275 eliminates noise according to the iterative operation based on the constraints generated by the aforementioned three constraint parts as described above. In other words, Function $E_{total}(I_1, I_2)$ given by Equation (6) is minimized, thereby calculating the separated images $I_1$ and $I_2$ from which noise has been eliminated.

[Equation 6]

$$E_{total}(I_1, I_2) = \arg\min_{I_1, I_2}\{\lambda_1 E_1(I_1, I_2) + \lambda_2 E_2(I_1, I_2) + \lambda_3 E_3(I_1, I_2)\} \qquad (6)$$

where $\lambda_1$, $\lambda_2$, and $\lambda_3$ are regularization parameters respectively adjusting the weights of the constraints $E_1$, $E_2$, and $E_3$. In the present embodiment, $\lambda_1$ and $\lambda_2$ are set as $\lambda_1=\lambda_2=1$, and $\lambda_3$ is adjusted as to each measured image, according to a publicly known method such as discrepancy principle. Alternatively, a fixed value may be used in response to an SNR that is estimated by measurement conditions. Further alternatively, a fixed value may be used in response to a standard deviation in the noise area of the measured images. According to step S1701 to S1704 as described so far, the noise elimination step S704 is completed.

[Display Image: S705]

The separated images after noise is eliminated, calculated by the noise eliminator 270, can be presented on the display 201 (FIG. 1). Alternatively, the external storage unit 203 stores the separated images as image data, and they may be displayed on a desired displaying unit.

According to the MRI apparatus and the image processing method of the present embodiment, computations for noise elimination are performed in the images acquired by using a plurality of receiver coils, using the noise correlation in the separated images as the constraints, and thereby enhancing the precision of noise elimination in the separated images and obtaining a high-quality image, then achieving improved accuracy in diagnosis. According to the present embodiment, the iterative operation is performed by using the constraints necessary for noise reduction, together with the noise correlation constraint, thereby preventing displacements of image from an original image and excessive smoothing, due to the noise elimination.

Modification 1 of the First Embodiment

In the first embodiment, there has been described an example that the noise elimination process is performed on the images separated according to the SENSE method for separating the spatially overlapping signals in the image space. However, this is not the only example. The noise elimination process as described in the first embodiment may also be applicable to other methods (such as SMASH method and GRAPPA method) where unmeasured data in k-space is estimated, by using the coil sensitivity distribution, to generate images (separated images) with no spatial aliasing.

Figure 11:
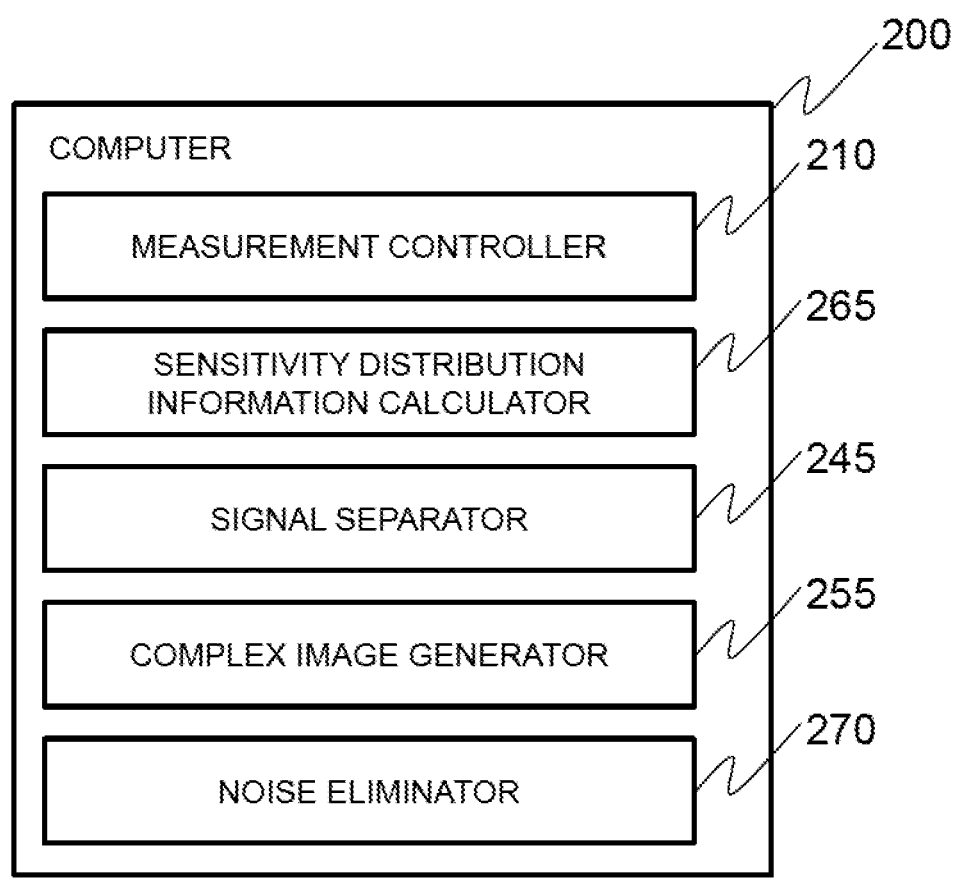
FIG. 11 is a functional block diagram of the computer according to a second embodiment.

In this case, as shown in FIG. 11, the image generator 230 (FIG. 1) comprises a signal separator 245 and a complex image generator 255. As in the case of the GRAPPA method, when the sensitivity distribution information corresponding to the sensitivity distributions of the receiver coils is calculated from the reference signal referred to as ACS (Auto Calibration Signal), a sensitivity distribution information calculator 265 is added. In the present modification, the signal separator 245 uses the k-space data of each receiver coil and the sensitivity distribution information of each receiver coil to form one k-space data, and the complex image generator 255 reconstructs an image by using thus formed k-space data. This reconstructed image comprises a plurality of images ($\rho_1$, $\rho_2$: separated images in FIG. 9) at spatially different positions, and thus the processing of the aforementioned noise eliminator 270 is performed on these separated images, so as to eliminate noise.

The present modification is different from the first embodiment in how to generate the separated images, and the same effect as the first embodiment can be obtained.

Modification 2 of the First Embodiment

According to the first embodiment, the sparse space constraint using the Wavelet transform is employed in the noise elimination process, in addition to the noise correlation constraint. Another type of sparse space transform can be used. For example, the sparse space transform using the discrete cosine transform or Total Variation (TV) may be used. Equation (7) defines the TV transform of any image I. In the present modification, the sparse constraint part 273 generates Equation (7) instead of Equation (5).

[Equation 7]

$$\|TV(I)\|_1 = |\nabla_x I| + |\nabla_y I| + |\nabla_z I| \qquad (7)$$

where $\nabla x$, $\nabla y$, and $\nabla z$ represent spatial gradients in x, y, and z directions, respectively. The iterative operation part 275 performs the iterative operation by using TV in Equation (7) as the function $E_3(I_1, I_2)$ in Equation (6), thereby minimizing noise. TV is a constraint indicating that noise in a spatial differential value image of the separated images is nearly zero, and using TV produces an effect of noise elimination that achieves local spatial smoothing.

Second Embodiment

In the first embodiment and the modifications thereof, noise elimination is performed on the separated images of an image including spatially overlapping signals, by thinning measurement (reduction measurement) of k-space data. In the present embodiment, according to SMS imaging that excites a plurality of slices simultaneously, separated images of an image where signals from a plurality of slices are overlapping are targeted for the noise elimination.

In the present embodiment, the imaging method is different from the first embodiment, but the method for separating spatially overlapping signals from an image obtained by imaging, is the same as the image separation using a plurality of receiver coils according to the SENSE method of the first embodiment. With reference to the figures that are used in describing the first embodiment, the present embodiment will now be described, focusing on a point different from the first embodiment.

FIG. 12(a) shows one example of the SMS pulse sequence employed in the present embodiment. FIG. 12(a) illustrates a fast spin-echo pulse sequence, called as TurboSpinEcho, FastSpinEcho, and others. RF pulses (180° RF pulses) are sequentially applied after application of 90° RF pulse for exciting a certain region on a subject. During this period, a readout gradient magnetic field is applied together with applying a phase-encoding gradient magnetic field, between adjacent inversion RF pulses, and an echo signal is measured. Varying the amount of the phase-encoding gradient magnetic field being applied for every echo, allows collection of data that fills the k-space in one or more times of excitation. In the SMS pulse sequence, the RF pulse and the gradient magnetic field pulse applied simultaneously with the RF pulse are different from those in a normal fast spin-echo pulse sequence that excites a single slice (portions surrounded by the dotted boxes in FIG. 12(a)). For example, in the CAIPIRINHA method being a typical SMS method, an RF pulse (MB: MultiBand pulse (FIG. 12(b)) is used, being the RF pulse where transmission frequencies are mixed, respectively associated with the positions of a plurality of slices simultaneously excited. During the application of this RF pulse, a slice-selective gradient magnetic field with constant strength is applied.

Assuming the number of slices excited simultaneously is N (N is an integer), the gradient magnetic field strength for exciting a desired slice thickness is G, and the position of the n-th slice is $z_n$, an RF pulse waveform RF(t) at the time t[sec] is expressed by the following equation (8):

[Equation 8]

$$RF_{sms}(t) = RF(t) \sum_{n=1}^{N} \exp(i2\pi G z_n t) \exp(\phi_n) \quad (8)$$

where $\varphi_n$ represents an initial phase when the n-th slice is excited. In the CAIPIRNHA method, when two slices (N=2) are measured simultaneously, by linearly varying the initial phase $\varphi_2$ of an RF pulse in the phase encoding direction, thereby shifting and measuring signals of the slices, within a field of view (FOV).

The SMS pulse sequence is not limited to the pulse sequence as described above. For example, the RF pulse may be not only an MB pulse, but also a combination of a pulse called as PINS (Power Independent of Number of Slice) pulse as shown in FIG. 12(c), and a blip-like slice gradient magnetic field, or a pulse such as a combination of the MB pulse and PINS pulse. Any of these pulses may be used.

Figure 13:
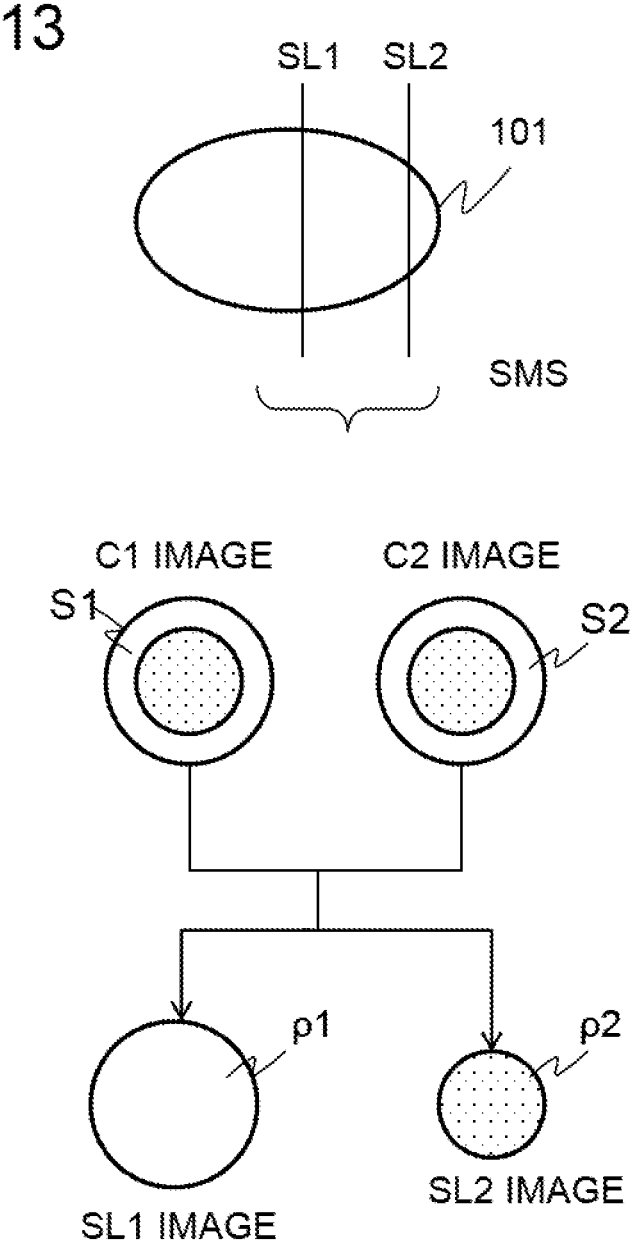
FIG. 13 illustrates one example of the spatially overlapping signals according to the second embodiment.

An echo generated by such pulse sequence as described above is measured, assuming that signals from a plurality of excited slices are combined. As shown in FIG. 13, for example, an image obtained by applying Fourier transform to the k-space data comprising those echoes, is an image where the image $S_1$ of the slice SL1 and the image $S_2$ of the slice SL2 are overlapping, when two slices SL1 and SL2 are excited simultaneously. From these images $S_1$ and $S_2$ obtained by the plurality of receiver coils, and by solving Equation (2) with the use of the sensitivity distributions C1 and C2 of the receiver coils, according to the first embodiment, images slice by slice, i.e., separated images ρ1 and ρ2 can be obtained.

Similar to the first embodiment, the noise eliminator 270 performs the noise elimination by the iterative operation using a plurality of constraints, on thus calculated separated images. In other words, as shown in FIG. 10, the iterative operation for minimizing the function as expressed by Equation (6) is performed, under the constraints including the constraint before and after noise elimination, the noise correlation constraint, and the sparse space constraints, thereby removing the noise in the separated images. Accordingly, it is possible to obtain a high quality image as to each slice from which noise has been eliminated.

The present embodiment can also be modified as appropriate, for example, applying the modification such as the modification 2 of the first embodiment (sparse space constraint using TV transform), to the constraint for noise elimination.

In the embodiments described so far, the noise elimination from the separated images obtained by separating spatially overlapping signals is executed in the computer incorporated in the MRI apparatus. In addition, the present invention includes that the noise elimination is executed in a computer or in an image processor, independent from the MRI apparatus. Furthermore, the scope of the present invention is to use the noises correlation between the separated images in eliminating noise from the separated images, and in the aforementioned embodiments, the present invention also includes addition or deletion of any elements, without departing from the scope of the invention.

DESCRIPTION OF SYMBOLS

10: MRI apparatus, 100: measuring part, 101: subject, 102: static magnetic field coil, 103: gradient coil, 104: shim coil, 105: transmit coil, 106: receiver coil, 107: transmitter, 108: receiver, 112: power supply for gradient magnetic field, 113: shim power supply, 114: sequence controller, 200: computer, 201: display, 203: external storage unit, 205: input unit, 210: measurement controller, 230: image generator, 240: complex image generator, 250: separated image calculator, 270: noise eliminator, 271: constraint part for image before and after noise elimination, 272: noise-correlation constraint part, 273: sparse constraint part, 275: iterative operation part, 290: display controller

The invention claimed is:

1. A noise elimination method for eliminating noise in an image created by using nuclear magnetic resonance signals measured by a plurality of receiver coils, the method comprising,
   generating a plurality of separated images not overlapping spatially, by using the nuclear magnetic resonance signals and sensitivity distributions of the plurality of receiver coils, and
   eliminating noise of each of the separated images on the basis of a noise correlation between the plurality of separated images.

2. The noise elimination method according to claim 1, wherein, the step of eliminating noise includes a step of performing an iterative operation process for minimizing noise, by using a constraint indicating that a sum image of the separated images before noise elimination is nearly equal to a sum image of the separated image after noise elimination.

3. A noise elimination method that eliminates noise in an image created by using nuclear magnetic resonance signals measured by a plurality of receiver coils, the method comprising the steps of, generating a complex image including spatially overlapping signals, separating the spatially overlapping signals by using sensitivity distributions of the plurality of receiver coils, and generating a plurality of separated images from the complex image, and eliminating noise in each of the separated images, based on a noise correlation between the plurality of separated images.

4. The noise elimination method according to claim 3, wherein, the step of eliminating noise includes a step of performing an iterative operation process for minimizing noise, by using a constraint indicating that a sum image of the separated images before noise elimination is nearly equal to a sum image of the separated images after noise elimination.

5. A magnetic resonance imaging apparatus comprising:

a measuring part including a transmission part, including a transmitter and a transmit coil, configured to transmit an RF pulse to a subject placed in a static magnetic field, a reception part, including a receiver and a receiver coil, configured to receive nuclear magnetic resonance signals generated from the subject by a plurality of receiver coils, and a gradient magnetic field generator, including a power supply and a gradient coil, configured to provide a gradient magnetic field to the static magnetic field, and a computer configured to perform computations on the nuclear magnetic resonance signals thus received, wherein, the computer comprises, an image generator configured to process the nuclear magnetic resonance signals received by the plurality of receiver coils to generate a plurality of separated images not spatially overlapping one another, by using sensitivity information of the plurality of receiver coils, and a noise eliminator configured to eliminate noise from each of the separated images, on the basis of a correlation of noise mixed between the separated images.

6. The magnetic resonance imaging apparatus, according to claim 5, wherein, the image generator comprises, a complex image generator configured to generate a complex image including spatially overlapping signals, by using the nuclear magnetic resonance signals, and a separated image calculator configured to separate the spatially overlapping signals of the complex image to calculate a plurality of separated images, by using the sensitivity information of the plurality of receiver coils.

7. The magnetic resonance imaging apparatus, according to claim 5, wherein, the noise eliminator comprises, a noise correlation constraint part configured to generate a constraint that a sum image of the separated images before noise elimination is nearly equal to a sum image of the separated images after noise elimination, and an iterative operation part configured to perform an iterative operation to minimize noise under limiting conditions including the constraint.

8. The magnetic resonance imaging apparatus, according to claim 7, wherein, the noise eliminator further includes at least one of the followings:

a constraint part for image before and after noise elimination configured to generate a constraint that the separated images before noise elimination are nearly equal to the separated images after noise elimination, and a sparse space constraint part configured to generate a constraint that noise in an image obtained by mapping the separated images in sparse space is nearly equal to zero.

9. The magnetic resonance imaging apparatus, according to claim 7, wherein, the noise eliminator further includes at least one of the followings:

a constraint part for image before and after noise elimination configured to generate a constraint that the separated images before noise elimination are nearly equal to the separated images after noise elimination, and a spatial differential value constraint part configured to generate a constraint that noise in a spatial differential value image of the separated images is nearly equal to zero.

10. The magnetic resonance imaging apparatus, according to claim 5, further comprising a measurement controller configured to control the measuring part according to an imaging sequence being predefined, wherein, the measurement controller controls an operation of the gradient magnetic field generator in such a manner that the magnetic resonance signals are measured in k-space while thinning is performed.

11. The magnetic resonance imaging apparatus, according to claim 5, further comprising a measurement controller configured to control the measuring part according to an imaging sequence being predefined, wherein, the measurement controller controls an operation of the transmission part and the gradient magnetic field generator in such a manner that nuclear magnetic resonance signals of slices at different positions in the subject are measured simultaneously.

12. The magnetic resonance imaging apparatus, according to claim 5, further comprising an input unit configured to accept a selection of noise elimination according to the noise eliminator.

* * * * *